United States Patent
Coughlin et al.

(10) Patent No.: US 7,999,049 B2
(45) Date of Patent: Aug. 16, 2011

(54) PROCESS FOR PRODUCING FLUOROELASTOMERS

(75) Inventors: Michael Cregg Coughlin, Wilmington, DE (US); Ming-Hong Hung, Wilmington, DE (US); Phan Linh Tang, West Chester, PA (US)

(73) Assignee: DuPont Performance Elastomers L.L.C., Wilmington, DE (US)

( * ) Notice: Subject to any disclaimer, the term of this patent is extended or adjusted under 35 U.S.C. 154(b) by 43 days.

(21) Appl. No.: 12/354,195

(22) Filed: Jan. 15, 2009

(65) Prior Publication Data

US 2009/0186997 A1    Jul. 23, 2009

Related U.S. Application Data

(60) Provisional application No. 61/011,850, filed on Jan. 22, 2008.

(51) Int. Cl.
*C08F 12/20* (2006.01)

(52) U.S. Cl. ........ 526/193; 524/711; 524/712; 524/805; 526/247; 526/249; 526/254; 526/255; 562/23; 562/25

(58) Field of Classification Search .......... 524/711, 524/712, 805; 526/179, 181, 193, 247, 249, 526/254, 255; 562/23, 25
See application file for complete search history.

(56) References Cited

U.S. PATENT DOCUMENTS

| | | | |
|---|---|---|---|
| 2,559,749 A | 7/1951 | Benning | |
| 2,559,752 A | 7/1951 | Berry | |
| 2,597,702 A | 5/1952 | Benning | |
| 3,467,635 A * | 9/1969 | Cleaver et al. | 526/255 |
| 4,214,060 A | 7/1980 | Apotheker et al. | |
| 4,281,092 A | 7/1981 | Breazeale | |
| 4,463,144 A * | 7/1984 | Kojima et al. | 526/94 |
| 5,738,802 A * | 4/1998 | Yamamoto et al. | 252/62.56 |
| 6,395,848 B1 | 5/2002 | Morgan et al. | |
| 6,512,063 B2 | 1/2003 | Tang | |
| 6,774,164 B2 | 8/2004 | Lyons et al. | |
| 2006/0229398 A1 | 10/2006 | Urban | |

FOREIGN PATENT DOCUMENTS

JP    2004358397 A    12/2004

OTHER PUBLICATIONS

U.S. Appl. No. 12/354,218, filed Jan. 15, 2009, Coughlin et al.

* cited by examiner

*Primary Examiner* — Mark Eashoo
*Assistant Examiner* — Nicole M Buie-Hatcher

(57) ABSTRACT

An emulsion polymerization process for the production of fluoroelastomers is disclosed wherein at least one fluorosurfactant is employed as dispersant, said fluorosurfactant being a fluoroalkylphosphoric acid ester of the formula $X-R_f-(CH_2)_n-O-P(O)(OM)_2$, wherein $n=1$ or 2, $X=H$ or F, $M=$a univalent cation, and $R_f$ is a $C_4$-$C_6$ fluoroalkyl or fluoroalkoxy group. Optionally, a second dispersing agent may be employed in the polymerization, said second agent being a perfluoropolyether having at least one endgroup selected from the group consisting of carboxylic acid, a salt thereof, sulfonic acid and a salt thereof, phosphoric acid and a salt thereof.

5 Claims, No Drawings

PROCESS FOR PRODUCING FLUOROELASTOMERS

CROSS-REFERENCE TO RELATED APPLICATIONS

This application claims the benefit of U.S. Provisional Application No. 61/011,850 filed Jan. 22, 2008.

FIELD OF THE INVENTION

This invention pertains to an emulsion polymerization process for the production of fluoroelastomers wherein at least one dispersing agent is employed, said dispersing agent being a fluoroalkylphosphoric acid ester of the formula X—Rf-$(CH_2)_n$—O—$P(O)(OM)_2$, wherein n=1 or 2, X=H or F, M=a univalent cation, and Rf is a $C_4$-$C_6$ fluoroalkyl or fluoroalkoxy group (branched or non-branched).

BACKGROUND OF THE INVENTION

Production of fluoroelastomers by emulsion and solution polymerization methods is well known in the art; see for example U.S. Pat. Nos. 4,214,060; 4,281,092; 6,512,063 and 6,774,164 B2. Generally, fluoroelastomers are produced in an emulsion polymerization process wherein a water-soluble polymerization initiator and a relatively large amount of dispersing agent (i.e. surfactant) are employed.

Benning (U.S. Pat. Nos. 2,559,749 and 2,597,702) discloses fluorinated aliphatic phosphates that may be employed as emulsifying agents in the aqueous polymerization of unsaturated organic compounds. These phosphate esters are said to be particularly useful in the polymerization of tetrafluoroethylene (TFE) and chlorotrifluoroethylene (CTFE) homopolymers.

Urban (U.S. Patent Application Publication 2006/0229398 A1) discloses the polymerization of fluoromonomers with (meth)acrylates in an aqueous system that employs both 1) a fluoroalkylphosphoric acid ester salt such as phosphoric acid bis(tridecafluorooctyl)ester ammonium salt, and 2) an anionic alkyl sulfonate surfactant such as sodium dodecyl sulfate.

Morgan et al. (U.S. Pat. No. 6,395,848 B1) disclose an aqueous dispersion process utilizing a combination of at least two fluorosurfactants. At least one surfactant is a perfluoropolyether (PFPE) carboxylic acid, sulfonic acid or the salt thereof and at least one surfactant is a fluoroalkyl carboxylic acid, sulfonic acid or the salt thereof, or a fluoroalkoxy aryl sulfonic acid or salt thereof.

SUMMARY OF THE INVENTION

One aspect of the present invention provides an emulsion polymerization process for the production of fluoroelastomers wherein the resulting fluoroelastomers are readily isolated from the emulsion. This process comprises polymerizing a first monomer selected from the group consisting of vinylidene fluoride, tetrafluoroethylene and perfluoro(methyl vinyl ether) with at least one different monomer in an aqueous medium comprising initiator and dispersing agent to obtain an aqueous dispersion of fluoroelastomer, wherein said dispersing agent is a fluoroalkylphosphoric acid ester of the formula X—Rf-$(CH_2)_n$—O—$P(O)(OM)_2$, wherein n=1 or 2, X=H or F, M=a univalent cation, and Rf is a $C_4$-$C_6$ fluoroalkyl or fluoroalkoxy group.

Another aspect of the invention is a dispersing agent having the formula $CF_3CF_2CF_2OCF(CF_3)(CH_2)_nOPO(OM)_2$ wherein n is 1 or 2, M is a univalent cation.

DETAILED DESCRIPTION OF THE INVENTION

The present invention is directed to an emulsion polymerization process for producing fluoroelastomers having a glass transition temperature of less than 20° C. The fluoroelastomer may be partially fluorinated or perfluorinated.

Fluoroelastomer polymers made by the process of this invention comprise copolymerized units of a first monomer selected from the group consisting of vinylidene fluoride, tetrafluoroethylene and perfluoro(methyl vinyl ether) with and at least one different monomer.

Fluoroelastomers made by the process of this invention preferably contain between 25 to 70 weight percent, based on the total weight of the fluoroelastomer, of copolymerized units of a first monomer which may be vinylidene fluoride ($VF_2$), perfluoro(methyl vinyl ether) (PMVE) or tetrafluoroethylene (TFE). The remaining units in the fluoroelastomers are comprised of one or more additional copolymerized monomers, different from said first monomer, selected from the group consisting of fluoromonomers, hydrocarbon olefins and mixtures thereof. Fluoromonomers include fluorine-containing olefins and fluorine-containing vinyl ethers.

Fluorine-containing olefins which may be employed to make fluoroelastomers by the present invention include, but are not limited to vinylidene fluoride ($VF_2$), hexafluoropropylene (HFP), tetrafluoroethylene (TFE), 1,2,3,3,3-pentafluoropropene (1-HPFP), 1,1,3,3,3-pentafluoropropene (2-HPFP), chlorotrifluoroethylene (CTFE) and vinyl fluoride.

Fluorine-containing vinyl ethers that may be employed to make fluoroelastomers by the present invention include, but are not limited to perfluoro(alkyl vinyl) ethers. Perfluoro (alkyl vinyl) ethers (PAVE) suitable for use as monomers include those of the formula $$CF_2=CFO(R_fO)_n(R_{f'}O)_mR_f \quad (I)$$

where $R_f$ and $R_{f'}$ are different linear or branched perfluoroalkylene groups of 2-6 carbon atoms, m and n are independently 0-10, and $R_f$ is a perfluoroalkyl group of 1-6 carbon atoms.

A preferred class of perfluoro(alkyl vinyl) ethers includes compositions of the formula $$CF_2=CFO(CF_2CFXO)_nR_f \quad (II)$$

where X is F or $CF_3$, n is 0-5, and $R_f$ is a perfluoroalkyl group of 1-6 carbon atoms.

A most preferred class of perfluoro(alkyl vinyl) ethers includes those ethers wherein n is 0 or 1 and $R_f$ contains 1-3 carbon atoms. Examples of such perfluorinated ethers include perfluoro(methyl vinyl ether) (PMVE), perfluoro(ethyl vinyl ether) (PEVE) and perfluoro(propyl vinyl ether) (PPVE). Other useful monomers include compounds of the formula $$CF_2=CFO[(CF_2)_mCF_2CFZO]_nR_f \quad (III)$$

where $R_f$ is a perfluoroalkyl group having 1-6 carbon atoms, m=0 or 1, n=0-5, and Z=F or $CF_3$. Preferred members of this class are those in which $R_f$ is $C_3F_7$, m=0, and n=1.

Additional perfluoro(alkyl vinyl) ether monomers include compounds of the formula $$CF_2=CFO[(CF_2CF\{CF_3\}O)_n(CF_2CF_2CF_2O)_m(CF_2)_p]C_xF_{2x+1} \quad (IV)$$

where m and n independently=0-10, p=0-3, and x=1-5. Preferred members of this class include compounds where n=0-1, m=0-1, and x=1.

Other examples of useful perfluoro(alkyl vinyl ethers) include $$CF_2=CFOCF_2CF(CF_3)O(CF_2O)_mC_nF_{2n+1} \quad (V)$$

where n=1-5, m=1-3, and where, preferably, n=1.

If copolymerized units of PAVE are present in fluoroelastomers prepared by the process of the invention, the PAVE content generally ranges from 25 to 75 weight percent, based on the total weight of the fluoroelastomer. If perfluoro(methyl vinyl ether) is used, then the fluoroelastomer preferably contains between 30 and 65 wt. % copolymerized PMVE units.

Hydrocarbon olefins useful in the fluoroelastomers prepared by the process of this invention include, but are not limited to ethylene and propylene. If copolymerized units of a hydrocarbon olefin are present in the fluoroelastomers prepared by the process of this invention, hydrocarbon olefin content is generally 4 to 30 weight percent.

The fluoroelastomers prepared by the process of the present invention may also, optionally, comprise units of one or more cure site monomers. Examples of suitable cure site monomers include, but are not limited to: i) bromine-containing olefins; ii) iodine-containing olefins; iii) bromine-containing vinyl ethers; iv) iodine-containing vinyl ethers; v) fluorine-containing olefins having a nitrile group; vi) fluorine-containing vinyl ethers having a nitrile group; vii) 1,1,3,3,3-pentafluoropropene (2-HPFP); viii) perfluoro(2-phenoxypropyl vinyl)ether; and ix) non-conjugated dienes.

Brominated cure site monomers may contain other halogens, preferably fluorine. Examples of brominated olefin cure site monomers are $CF_2=CFOCF_2CF_2CF_2OCF_2CF_2Br$; bromotrifluoroethylene; 4-bromo-3,3,4,4-tetrafluorobutene-1 (BTFB); and others such as vinyl bromide, 1-bromo-2,2-difluoroethylene; perfluoroallyl bromide; 4-bromo-1,1,2-trifluorobutene-1; 4-bromo-1,1,3,3,4,4-hexafluorobutene; 4-bromo-3-chloro-1,1,3,4,4-pentafluorobutene; 6-bromo-5,5,6,6-tetrafluorohexene; 4-bromoperfluorobutene-1 and 3,3-difluoroallyl bromide. Brominated vinyl ether cure site monomers useful in the invention include 2-bromo-perfluoroethyl perfluorovinyl ether and fluorinated compounds of the class $CF_2Br—R_f—O—CF=CF_2$ ($R_f$ is a perfluoroalkylene group), such as $CF_2BrCF_2O—CF=CF_2$, and fluorovinyl ethers of the class $ROCF=CFBr$ or $ROCBr=CF_2$ (where R is a lower alkyl group or fluoroalkyl group) such as $CH_3OCF=CFBr$ or $CF_3CH_2OCF=CFBr$.

Suitable iodinated cure site monomers include iodinated olefins of the formula: $CHR=CH—Z—CH_2CHR—I$, wherein R is —H or —$CH_3$; Z is a $C_1$-$C_{18}$ (per)fluoroalkylene radical, linear or branched, optionally containing one or more ether oxygen atoms, or a (per)fluoropolyoxyalkylene radical as disclosed in U.S. Pat. No. 5,674,959. Other examples of useful iodinated cure site monomers are unsaturated ethers of the formula: $I(CH_2CF_2CF_2)_nOCF=CF_2$ and $ICH_2CF_2O[CF(CF_3)CF_2O]_nCF=CF_2$, and the like, wherein n=1-3, such as disclosed in U.S. Pat. No. 5,717,036. In addition, suitable iodinated cure site monomers including iodoethylene, 4-iodo-3,3,4,4-tetrafluorobutene-1 (ITFB); 3-chloro-4-iodo-3,4,4-trifluorobutene; 2-iodo-1,1,2,2-tetrafluoro-1-(vinyloxy)ethane; 2-iodo-1-(perfluorovinyloxy)-1,1,-2,2-tetrafluoroethylene; 1,1,2,3,3,3-hexafluoro-2-iodo-1-(perfluorovinyloxy)propane; 2-iodoethyl vinyl ether; 3,3,4,5,5,5-hexafluoro-4-iodopentene; and iodotrifluoroethylene are disclosed in U.S. Pat. No. 4,694,045. Allyl iodide and 2-iodo-perfluoroethyl perfluorovinyl ether are also useful cure site monomers.

Useful nitrile-containing cure site monomers include those of the formulas shown below.

$$CF_2=CF—O(CF_2)_n—CN \quad (VI)$$

where n=2-12, preferably 2-6;

$$CF_2=CF—O[CF_2—CF(CF_3)—O]_n—CF_2—CF(CF_3)—CN \quad (VII)$$

where n=0-4, preferably 0-2;

$$CF_2=CF—[OCF_2CF(CF_3)]_x—O—(CF_2)_n—CN \quad (VIII)$$

where x=1-2, and n=1-4; and $$CF_2=CF—O—(CF_2)_n—O—CF(CF_3)CN \quad (IX)$$

where n=2-4. Those of formula (VIII) are preferred. Especially preferred cure site monomers are perfluorinated polyethers having a nitrile group and a trifluorovinyl ether group. A most preferred cure site monomer is $$CF_2=CFOCF_2CF(CF_3)OCF_2CF_2CN \quad (X)$$

i.e. perfluoro(8-cyano-5-methyl-3,6-dioxa-1-octene) or 8-CNVE.

Examples of non-conjugated diene cure site monomers include, but are not limited to 1,4-pentadiene; 1,5-hexadiene; 1,7-octadiene; 3,3,4,4-tetrafluoro-1,5-hexadiene; and others, such as those disclosed in Canadian Patent 2,067,891 and European Patent 0784064A1. A suitable triene is 8-methyl-4-ethylidene-1,7-octadiene.

Of the cure site monomers listed above, preferred compounds, for situations wherein the fluoroelastomer will be cured with peroxide, include 4-bromo-3,3,4,4-tetrafluorobutene-1 (BTFB); 4-iodo-3,3,4,4-tetrafluorobutene-1 (ITFB); allyl iodide; bromotrifluoroethylene and a nitrile-containing cure site monomer such as 8-CNVE. When the fluoroelastomer will be cured with a polyol, 2-HPFP or perfluoro(2-phenoxypropyl vinyl) ether is the preferred cure site monomer. When the fluoroelastomer will be cured with a tetraamine, bis(aminophenol) or bis(thioaminophenol), a nitrile-containing cure site monomer (e.g. 8-CNVE) is the preferred cure site monomer. When the fluoroelastomer will be cured with ammonia or a compound that releases ammonia at curing temperatures (e.g. urea), a nitrile-containing cure site monomer (e.g. 8-CNVE) is the preferred cure site monomer.

Units of cure site monomer, when present in the fluoroelastomers manufactured by the process of this invention, are typically present at a level of 0.05-10 wt. % (based on the total weight of fluoroelastomer), preferably 0.05-5 wt. % and most preferably between 0.05 and 3 wt. %.

Specific fluoroelastomers which may be produced by the process of this invention include, but are not limited to those comprising copolymerized units of i) vinylidene fluoride and hexafluoropropylene; ii) vinylidene fluoride, hexafluoropropylene and tetrafluoroethylene; iii) vinylidene fluoride, hexafluoropropylene, tetrafluoroethylene and 4-bromo-3,3,4,4-tetrafluorobutene-1; iv) vinylidene fluoride, hexafluoropropylene, tetrafluoroethylene and 4-iodo-3,3,4,4-tetrafluorobutene-1; v) vinylidene fluoride, perfluoro(methyl vinyl ether), tetrafluoroethylene and 4-bromo-3,3,4,4-tetrafluorobutene-1; vi) vinylidene fluoride, perfluoro(methyl vinyl ether), tetrafluoroethylene and 4-iodo-3,3,4,4-tetrafluorobutene-1; vii) vinylidene fluoride, perfluoro(methyl vinyl ether), tetrafluoroethylene and 1,1,3,3,3-pentafluoropropene; viii) tetrafluoroethylene, perfluoro(methyl vinyl ether) and ethylene; ix) tetrafluoroethylene, perfluoro(methyl vinyl ether), ethylene and 4-bromo-3,3,4,4-tetrafluorobutene-1; x) tetrafluoroethylene, perfluoro(methyl vinyl ether), ethylene and 4-iodo-3,3,4,4-tetrafluorobutene-1; xi) tetrafluoroethylene, propylene and vinylidene fluoride; xii) tetrafluoroethylene and perfluoro(methyl vinyl ether); xiii) tetrafluoroethylene, perfluoro(methyl vinyl ether) and perfluoro(8-cyano-5-methyl-3,6-dioxa-1-octene); xiv) tetrafluoroethylene, perfluoro(methyl vinyl ether) and 4-bromo-3,3,4,4-tetrafluorobutene-1; xv) tetrafluoroethylene, perfluoro(methyl vinyl ether) and 4-iodo-3,3,4,4-tetrafluorobutene-1; xvi) tetrafluoroethylene, perfluoro(methyl vinyl ether) and perfluoro(2-phenoxypropyl vinyl) ether; and xvii) tetrafluoroethylene and propylene.

Additionally, iodine-containing endgroups, bromine-containing endgroups or mixtures thereof may optionally be present at one or both of the fluoroelastomer polymer chain ends as a result of the use of chain transfer or molecular weight regulating agents during preparation of the fluoroelastomers. The amount of chain transfer agent, when employed, is calculated to result in an iodine or bromine level in the fluoroelastomer in the range of 0.005-5 wt. %, preferably 0.05-3 wt. %.

Examples of chain transfer agents include iodine-containing compounds that result in incorporation of a bound iodine atom at one or both ends of the polymer molecules. Methylene iodide; 1,4-diiodoperfluoro-n-butane; and 1,6-diiodo-3,3,4,4,tetrafluorohexane are representative of such agents. Other iodinated chain transfer agents include 1,3-diiodoperfluoropropane; 1,6-diiodoperfluorohexane; 1,3-diiodo-2-chloroperfluoropropane; 1,2-di(iododifluoromethyl)-perfluorocyclobutane; monoiodoperfluoroethane; monoiodoperfluorobutane; 2-iodo-1-hydroperfluoroethane, etc. Also included are the cyano-iodine chain transfer agents disclosed in European Patent 0868447A1. Particularly preferred are diiodinated chain transfer agents.

Examples of brominated chain transfer agents include 1-bromo-2-iodoperfluoroethane; 1-bromo-3-iodoperfluoropropane; 1-iodo-2-bromo-1,1-difluoroethane and others such as disclosed in U.S. Pat. No. 5,151,492.

Other chain transfer agents suitable for use in the process of this invention include those disclosed in U.S. Pat. No. 3,707,529. Examples of such agents include isopropanol, diethylmalonate, ethyl acetate, carbon tetrachloride, acetone and dodecyl mercaptan.

Cure site monomers and chain transfer agents may be added to the reactor neat or as solutions. In addition to being introduced into the reactor near the beginning of polymerization, quantities of chain transfer agent may be added throughout the entire polymerization reaction period, depending upon the desired composition of the fluoroelastomer being produced, the chain transfer agent being employed, and the total reaction time.

The dispersing agent employed in the emulsion polymerization of this invention is a fluoroalkylphosphoric acid ester of the formula X—Rf-$(CH_2)_n$—O—P(O)$(OM)_2$, wherein n is 1 or 2 (preferably 1), X=H or F, M=a univalent cation, preferably H, Na, K, Li, or $NH_4$, and Rf is a $C_4$-$C_6$ fluoroalkyl or fluoroalkoxy group. The fluoroalkyl and fluoroalkoxy groups may be branched or non-branched. Preferably, the fluoroalkyl and fluoroalkoxy groups are perfluorinated. Each M need not be the same. For example, depending on pH of the aqueous solution containing the dispersing agent, one M may be H while the other M is $NH_4$, Na, Li or K.

Specific examples of such dispersing agents include, but are not limited to $CF_3CF_2CF_2OCF(CF_3)(CH_2)_nOPO(OM)_2$, H—$(CF_2)_6$—$CH_2$—O—P(O)$(OM)_2$ and F—$(CF_2)_5$—$CH_2$—O—P(O)$(OM)_2$. M=H or $NH_4$ are preferred. $CF_3CF_2CF_2OCF(CF_3)(CH_2)_nOPO(OH)_2$ and $CF_3CF_2CF_2OCF(CF_3)(CH_2)_nOPO(OH)(ONH_4)$ are especially preferred. In the latter two dispersing agents, n is preferably 1.

Optionally, a second dispersing agent (in addition to the fluoroalkylphosphoric acid esters described above) may be employed in the polymerization process of the invention. In this aspect of the invention, the second dispersing agent is a perfluoropolyether (PFPE) having at least one endgroup selected from the group consisting of carboxylic acid, carboxylic acid salt, sulfonic acid, sulfonic acid salt, phosphoric acid and phosphoric acid salt. The perfluoropolyether used in this invention can have any chain structure in which oxygen atoms in the backbone of the molecule are separated by saturated fluorocarbon groups having 1-3 carbon atoms. More than one type of fluorocarbon group may be present in the molecule. Representative structures have the repeat unit

    (XI)

    (XII)

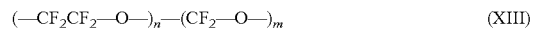    (XIII)

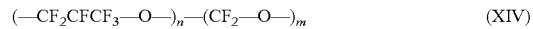    (XIV)

These structures are discussed by Kasai in J. Appl. Polymer Sci. 57, 797 (1995). As disclosed therein, such PFPE can have a carboxylic acid group or salt thereof ("carboxylic group") at one end or at both ends. Such structures are also possible with sulfonic groups or phosphoric groups at one end or at both ends. The "sulfonic" group or "phosphoric" group may be present as the acid or as its ionic salt. In addition, PFPE with acid functionality at both ends may have a carboxylic group at one end and a sulfonic group at the other. The PFPE-sulfonic acids are produced by bubbling $SO_2$ through a solution of the corresponding potassium PFPE carboxylates in dimethylformamide at 140° C. following by extraction and conversion to the acid form by ion exchange. PFPE-phosphoric acids are made by first reducing the PFPE-carboxylic acid or PFPE-acid fluoride to the alcohol and then the alcohol is reacted with either $POCl_3$, followed by hydrolysis in water, or the alcohol is reacted with $P_2O_5$. PFPE having structure XI is available from DuPont. PFPE having structure XII is available from Daikin. PFPE-XIII and XIV are available from Solvay Solexis. The PFPEs useful in the present invention are not limited to the particular PFPEs available from these companies. For monocarboxyl, monosulfonic, or monophosphoric PFPE, the other end of the molecule is usually perfluorinated but may contain a hydrogen or chlorine atom. PFPE having a carboxyl, sulfonic, or phosphoric group at one or both ends that can be used in the present invention have at least 2 ether oxygens, more preferably at least 4 ether oxygens, and even more preferably at least 6 ether oxygens. Preferably, at least one of the fluorocarbon groups separating ether oxygens, and more preferably at least two of such fluorocarbon groups, has 2 or 3 carbon atoms. Even more preferably, at least 50% of the fluorocarbon groups separating ether oxygens has 2 or 3 carbon atoms. Also, preferably, the PFPE has a total of at least 9 carbon atoms, whereby the minimum value of n and n+m in the above repeat unit structures is at least 3. The molecular weight is low enough so that the PFPE is normally liquid at room temperature. While more than one PFPE having a carboxyl, sulfonic, or phosphoric group at one or both ends can be used, normally only one such PFPE is employed.

The amount of total dispersing agent (i.e. amount of fluoroalkylphosphoric acid ester, plus the amount of optional PFPE (if any)) employed in the process of the invention is within typical ranges. Thus, the amount of total dispersing agent can be from about 0.01 wt. % to about 10 wt. %, preferably 0.05-7 wt. %, based on the total weight of water used in the polymerization. The concentration of dispersing agents that may be employed in the polymerization process of the present invention may be above or below the critical micelle concentration (c.m.c.) of each dispersing agent. The c.m.c. is different for different dispersing agents. As one skilled in the art will recognize, the amount of dispersing agent required to achieve a given level of dispersion stability will increase with the amount of polymer to be made at constant particle size. The amount of dispersing agent required for stability also increases with decreasing particle diameter at constant amount of polymer made, since total surface area increases under these conditions. This is observed in some instances for the process of the present invention, which generally yields smaller dispersion particles than a similar process carried out in the absence of PFPE having carboxyl, phosphoric or sulfonic ends. In such instances, if total dispersing agent is not increased, the resultant dispersion can be unstable at room temperature and form a gel. However, the dispersions of this invention are still more stable at room temperature than would be expected from their total dispersing agent level and with their small dispersion particle size. Surprisingly, resultant dispersions that are unstable at room temperature appear to be stable at elevated temperatures used in polymerization, as judged by the small amount of coagulum in the reactor. "Coagulum" is non-water-wettable polymer that can separate from the aqueous dispersion during polymerization. The amount of coagulum formed is an indicator of dispersion stability.

While PFPE having carboxyl, phosphoric or sulfonic ends may be present in major amount in the dispersing agent, such compounds are costly. Of the total dispersing agent, optional PFPE having carboxyl, phosphoric or sulfonic end groups preferably is present in minor amount, i.e., less than half of total dispersing agent by weight. The amount of PFPE having carboxyl, phosphoric or sulfonic ends is more preferably no more than 25 wt. %, most preferably no more than 15 wt. %, based on weight of total dispersing agent. When present, the amount of optional PFPE having carboxyl, phosphoric or sulfonic ends is at least 1 wt. %, preferably at least 3 wt. %, based on the weight of total dispersing agent. The amount of PFPE having carboxyl, phosphoric or sulfonic endgroups that is used will depend on the level of effect (i.e., the particle size) desired. Surprisingly, the use of PFPE having carboxyl, phosphoric or sulfonic ends alone, e.g., in the absence of fluoroalkylphosphoric acid ester dispersing agent, does not yield improved results compared to the use of fluoroalkylphosphoric acid ester dispersing agent alone. That is, the use of a combination of at least two dispersing agents, at least one of the dispersing agents being a fluoroalkylphosphoric acid ester and at least one of the dispersing agents being a perfluoropolyether carboxylic acid, phosphoric acid, or sulfonic acid or salt thereof provides a synergistic effect to the polymerization process, as compared to the use of either type of dispersing agent alone.

As used herein, "combination of dispersing agents" means that the components of the "combination" are present in the reactor during polymerization. The components can be introduced separately, including at different times, and need not be physically combined prior to introduction into the reactor, although they may be so combined. In batch polymerization, all of the dispersing agent may be added to the reactor before polymerization is begun or the addition can be split between a reactor precharge and a later addition, typically after most of the particle nucleation has occurred. The addition of the optional PFPE is preferably with the precharge. In continuous polymerization, dispersing agent components are preferably added as a mixture, typically throughout the polymerization.

The emulsion polymerization process of this invention may be a continuous, semi-batch or batch process. In any process, one or more monomers may optionally be pre-emulsified with dispersing agent to produce a microemulsion having monomer droplet size less than 10 microns. A high shear mixer is typically employed to form the microemulsion.

In the semi-batch emulsion polymerization process of this invention, a gaseous monomer mixture of a desired composition (initial monomer charge) is introduced into a reactor which contains an aqueous medium precharge. The reactor is typically not completely filled with the aqueous medium, so that a vapor space remains. The aqueous medium comprises at least one dispersing agent of the types discussed above, i.e. a fluoroalkylphosphoric acid ester and, optionally, a PFPE having a carboxyl, phosphoric or sulfonic endgroup. Optionally, the aqueous medium may contain a pH buffer, such as a phosphate or acetate buffer for controlling the pH of the polymerization reaction. Instead of a buffer, a base, such as NaOH may be used to control pH. Generally, pH is controlled to between 1 and 7 (preferably 3-7), depending upon the type of fluoroelastomer being made. Alternatively, or additionally, pH buffer or base may be added to the reactor at various times throughout the polymerization reaction, either alone or in combination with other ingredients such as polymerization initiator, liquid cure site monomer, chain transfer agent, or dispersing agent. If only the optional PFPE type dispersing agent is present in the reactor precharge, the phosphoric acid ester type fluorosurfactant dispersing agent is added during the polymerization reaction. Also optionally, the initial aqueous medium may contain a water-soluble inorganic peroxide polymerization initiator.

The initial monomer charge contains a quantity of a first monomer of either TFE, PMVE or $VF_2$ and also a quantity of one or more additional monomers which are different from the first monomer. The amount of monomer mixture contained in the initial charge is set so as to result in a reactor pressure between 0.5 and 10 MPa.

The monomer mixture is dispersed in the aqueous medium and, optionally, a chain transfer agent may also be added at this point while the reaction mixture is agitated, typically by mechanical stirring. In the initial gaseous monomer charge, the relative amount of each monomer is dictated by reaction kinetics and is set so as to result in a fluoroelastomer having the desired ratio of copolymerized monomer units (i.e. very slow reacting monomers must be present in a higher amount relative to the other monomers than is desired in the composition of the fluoroelastomer to be produced).

The temperature of the semi-batch reaction mixture is maintained in the range of 25° C.-130° C., preferably 50° C.-100° C. Polymerization begins when the initiator either thermally decomposes or reacts with reducing agent and the resulting radicals react with dispersed monomer.

Additional quantities of the gaseous monomer(s) and optional cure site monomer (incremental feed) are added at a controlled rate throughout the polymerization in order to maintain a constant reactor pressure at a controlled temperature. The relative ratio of monomers contained in the incremental feed is set to be approximately the same as the desired ratio of copolymerized monomer units in the resulting fluoroelastomer. Thus, the incremental feed contains between 25 to 70 weight percent, based on the total weight of the monomer mixture, of a first monomer of either TFE, PMVE or $VF_2$ and 75 to 30 weight percent total of one or more additional monomers that are different from the first monomer. Chain transfer agent may also, optionally, be introduced into the reactor at any point during this stage of the polymerization. Additional dispersing agent(s) and polymerization initiator may also be fed to the reactor during this stage. The amount of polymer formed is approximately equal to the cumulative amount of incremental monomer feed. One skilled in the art will recognize that the molar ratio of monomers in the incremental feed is not necessarily exactly the same as that of the desired (i.e. selected) copolymerized monomer unit composition in the resulting fluoroelastomer because the composition of the initial charge may not be exactly that required for the selected final fluoroelastomer composition, or because a portion of the monomers in the incremental feed may dissolve into the polymer particles already formed, without reacting. Polymerization times in the range of from 2 to 30 hours are typically employed in this semi-batch polymerization process.

The continuous emulsion polymerization process of this invention differs from the semi-batch process in the following manner. The reactor is completely filled with aqueous medium so that there is no vapor space. Gaseous monomers and solutions of other ingredients such as water-soluble monomers, chain transfer agents, buffer, bases, polymerization initiator, dispersing agent, etc., are fed to the reactor in separate streams at a constant rate. Feed rates are controlled so that the average polymer residence time in the reactor is generally between 0.2 to 4 hours. Short residence times are employed for reactive monomers, whereas less reactive monomers such as perfluoro(alkyl vinyl) ethers require more time. The temperature of the continuous process reaction mixture is maintained in the range of 25° C.-130° C., preferably 70° C.-120° C.

In the process of this invention, the polymerization temperature is maintained in the range of 25°-130° C. If the temperature is below 25° C., the rate of polymerization is too slow for efficient reaction on a commercial scale, while if the temperature is above 130° C., the reactor pressure required in order to maintain polymerization is too high to be practical.

The polymerization pressure is controlled in the range of 0.5 to 10 MPa, preferably 1 to 6.2 MPa. In a semi-batch process, the desired polymerization pressure is initially achieved by adjusting the amount of gaseous monomers in the initial charge, and after the reaction is initiated, the pressure is adjusted by controlling the incremental gaseous monomer feed. In a continuous process, pressure is adjusted by means of a back-pressure regulator in the dispersion effluent line. The polymerization pressure is set in the above range because if it is below 1 MPa, the monomer concentration in the polymerization reaction system is too low to obtain a satisfactory reaction rate. In addition, the molecular weight does not increase sufficiently. If the pressure is above 10 MPa, the cost of the required high pressure equipment is very high.

The amount of fluoroelastomer formed is approximately equal to the amount of incremental feed charged, and is in the range of 10-35 parts by weight of fluoroelastomer per 100 parts by weight of aqueous emulsion, preferably in the range of 20-30 parts by weight of the fluoroelastomer. The degree of fluoroelastomer formation is set in the above range because if it is less than 10 parts by weight, productivity is undesirably low, while if it is above 35 parts by weight, the solids content becomes too high for satisfactory stirring.

Water-soluble peroxides which may be used to initiate polymerization in this invention include, for example, the ammonium, sodium or potassium salts of hydrogen persulfate. In a redox-type initiation, a reducing agent such as sodium sulfite, is present in addition to the peroxide. These water-soluble peroxides may be used alone or as a mixture of two or more types. The amount to be used is selected generally in the range of 0.01 to 0.4 parts by weight per 100 parts by weight of polymer, preferably 0.05 to 0.3. During polymerization some of the fluoroelastomer polymer chain ends are capped with fragments generated by the decomposition of these peroxides.

Optionally, fluoroelastomer gum or crumb may be isolated from the fluoroelastomer dispersions produced by the process of this invention by the addition of a coagulating agent to the dispersion. Any coagulating agent known in the art may be used. Preferably, a coagulating agent is chosen which forms a water-soluble salt with the dispersing agent contained in the dispersion. Otherwise, precipitated dispersing agent salt may become entrained in the isolated fluoroelastomer and then retard curing of the fluoroelastomer with bisphenol-type curatives.

Common coagulants include, but are not limited to aluminum salts (e.g. potassium aluminum sulfate), calcium salts (e.g. calcium nitrate), magnesium salts (e.g. magnesium sulfate), or mineral acids (e.g. nitric acid). Salts of calcium, magnesium, or univalent cations with such short chain surfactants are water-soluble, and thus readily removable from the fluoroelastomer.

Instead of employing a coagulant, fluoroelastomers produced by this invention may be mechanically or freeze-thaw coagulated.

The fluoroelastomers prepared by the process of this invention are useful in many industrial applications including seals, wire coatings, tubing and laminates.

EXAMPLES

Test Methods

Mooney viscosity, ML (1+10), was determined according to ASTM D1646 with an L (large) type rotor at 121° C., using a preheating time of one minute and rotor operation time of 10 minutes.

The invention is further illustrated by, but is not limited to, the following examples.

Fluoroalkylphosphoric acid esters suitable for use in the emulsion polymerization process of this invention were prepared by the following procedures.

Preparation of 2,2,3,3,4,4,5,5,6,6,7,7-Dodecafluoro-1-Heptanephosphoric Acid Ester [H(CF$_2$)$_6$—CH$_2$O—PO(OH)$_2$]

In the first step, the phosphorodichloridate was prepared from the fluoroalkyl alcohol. Into a reaction flask equipped with condenser and temperature probe was added 1H,1H,7H-perfluoroheptane-1-ol (150 grams, 0.45 moles) and calcium chloride (10.2 grams, 0.092 moles). While stirring the contents under nitrogen, phosphorus oxychloride (207.3 grams, 1.35 moles) was added to the flask. The temperature of the contents dropped from ambient to about 15° C. The reaction mixture was then heated to 110° C. for 6 hours.

After the reaction was completed (as confirmed by gas chromatography), excess phosphorus oxychloride was distilled off (bp. 105° C.). Further vacuum distillation afforded the desired phosphorodichloridate product as a clear, colorless liquid. Bp. 95° C./0.3 mmHg. Yield=158-170 g.

$^1$H-NMR (400 MHz, acetone-d$_6$): δ6.83 (tt, J=51 Hz, 5.2 Hz, 1H), 5.20 (m, 2H);

$^{19}$F-NMR (376.89 MHz, acetone-d$_6$): −119.4 (m, 2F), −121.7 (m, 2F), −122.4 (m, 2F), −122.9 (m, 2F), −129.1 (m, 2F), −138.0 (dm, J=51 Hz, 2F).

In a second step, the phosphorodichloridate was hydrolyzed to yield the fluoroalkylphosphoric acid ester. In a round bottomed flask was charged 1H,1H,7H-perfluoroheptane-1-ol, phosphorodichloridate (158 grams, 0.352 moles) prepared above. Water (12.78 grams, 0.71 moles) was added dropwise while the temperature was maintained between 35° and 45°

C. (external ice-water cooling). After addition was completed, the reaction mixture was stirred at ambient temperature for 3 hours. The resulting solution was put under high vacuum at 45°-50° C., resulting in a white solid product. Yield was quantitative.

$^1$H-NMR (400 MHz, acetone-$d_6$): δ9.68 (S, —OH's), 6.82 (tt, J=51 Hz, 10.5 Hz, 1H), 4.61 (m, 2H);
$^{19}$F-NMR (376.89 MHz, acetone-$d_6$): −120.5 (m, 2F), −122.1 (m, 2F), −123.1 (m, 2F), −123.3 (m, 2F), −129.5 (m, 2F), −138.4 (dm, J=51 Hz, 2F).

Preparation of 2,2,3,3,4,4,5,5,6,6,6-Undecafluoro-1-Hexaphosphoric Acid Ester [F(CF$_2$)$_5$—CH$_2$O—PO(OH)$_2$]

In the first step, the phosphorodichloridate was prepared from the fluoroalkyl alcohol. In a reaction flask equipped with condenser and temperature probe was added 1H,1H-perfluorohexane-1-ol (50 grams, 0.166 moles) and calcium chloride (2.9 grams, 0.026 moles). While stirring the flask contents under nitrogen, phosphorus oxychloride (207 grams, 1.35 moles) was added slowly to the alcohol. The reaction mixture was then heated to 110° C. for 5 hours.

After the reaction was completed, excess phosphorus oxychloride was distilled off. Further vacuum distillation afforded the desired phosphorodichloridate product as a clear, colorless liquid. Bp. 88°-90° C./5 mm Hg. Yield=53.3 g.

$^1$H-NMR (400 MHz, acetone-$d_6$): δ5.25 (m, 2H);
$^{19}$F-NMR (376.89 MHz, acetone-$d_6$): −80.7 (m, 3F), −119.3 (m, 2F), −122.4 (m, 4F), −125.7 (m, 2F)

In a second step, the phosphorodichloridate was hydrolyzed to yield the fluoroalkylphosphoric acid ester. Into a round bottomed flask was charged 1H,1H-perfluorohexane-1-ol, phosphorodichloridate (83.4 grams, 0.20 moles). Water (7.2 grams, 0.40 moles) was added dropwise while the temperature was maintained between 35° and 45° C. (external ice-water cooling). After addition was completed, the reaction mixture was stirred at ambient temperature for 2 hours. The solution was then put under high vacuum at 60° C. to dry, resulting in a white solid product. Yield was 75.9 grams.

$^1$H-NMR (400 MHz, acetone-$d_6$): δ4.60 (m, 2H);
$^{19}$F-NMR (376.89 MHz, acetone-$d_6$): −82.2 (m, 3F), −121.5 (m, 2F), −123.9 (m, 2F), −124.0 (m, 2F), −127.3 (m, 2F).

Preparation of 2-Trifluoromethyl-3-oxa-2,4,4,5,5,6,6,6-octafluorohexanoyl Phosphoric Acid Ester [CF$_3$CF$_2$CF$_2$OCF(CF$_3$)CH$_2$OPO(OH)$_2$]

In the first step, the fluoroalkyl alcohol was prepared from 2-trifluoromethyl-3-oxa-2,4,4,5,5,6,6,6-octafluorohexanoyl fluoride (i.e. HFPO dimer, commercially available from DuPont). In a reaction flask equipped with condenser and temperature probe was charged LiAlH$_4$ (13.5 g, 0.355 moles) and 500 ml ether solvent and the contents cooled to 0° C. (NaBH$_4$ may be employed in place of LiAlH$_4$). HFPO-dimer (149.4 g, 0.45 moles) was added slowly and the reaction flask contents temperature was controlled at <10° C. with external cooling. After the addition was completed, the reaction mixture was stirred for 2-3 hours at 5-10° C. The reaction mixture was slowly transferred into a 400 ml 6 N HCl/500 mL ice water mixture and the ether layer was separated. The bottom layer was extracted with 200 mL ether (twice). The ether layers were combined, dried over magnesium sulfate, and then distilled to give the fluoroalcohol 2-trifluoromethyl-3-oxa-2,4,4,5,5,6,6,6-octafluorohexane-1-ol (HFPO dimer alcohol) as a clear, colorless liquid, Bp. 112°-114° C. Yield: 127 grams (89%).

$^1$H-NMR (400 MHz, acetone-$d_6$): δ 4.30 (m);
$^{19}$F-NMR (376.89 MHz, acetone-$d_6$): −80.5 to −82.5 (m, 8F), −129.4 (m, 2F), −134.6 (dm, 1F).

In the second step, the phosphorodichloridate 2-trifluoromethyl-3-oxa-2,4,4,5,5,6,6,6-octafluoro-hexanoyl phosphorodichloridic acid (HFPO dimer phosphoryl chloride) was prepared from the fluoroalkyl alcohol. In a reaction flask equipped with condenser and temperature probe was charged phosphorus oxychloride (255.1 g, 1.662 moles) and calcium chloride (7.14 g, 0.064 moles). While stirring the flask contents under nitrogen, HFPO dimer alcohol (127 g, 0.402 moles) was added in several large portions. The temperature of the contents dropped several degrees. The reaction mixture was heated at 105°-110° C. for 6 hours. The reaction progress was monitored by GC.

After the reaction was completed, excess phosphorus oxychloride was distilled off (Bp. 105° C.). Further vacuum distillation afforded the desired phosphorodichloridate as a clear, colorless liquid. Bp. 35°-38° C./2-3 mm Hg (or 59° C./4.2 mm Hg). Yield was approximately 105 grams (60%).

$^{19}$F-NMR (376.89 MHz, acetone-$d_6$): −80.5 to −82.5 (m, 8F), −129.4 (m, 2F), −135.1 (dm, 1F).

In the third step, the phosphorodichloridate was hydrolyzed to yield the fluoroalkylphosphoric acid ester 2-trifluoromethyl-3-oxa-2,4,4,5,5,6,6,6-octafluorohexanoyl phosphoric acid ester. In a round bottom flask was charged the HFPO dimer phosphoryl chloride prepared above (105 g, 0.242 moles). Water (9.8 g, 0.544 moles) was added dropwise while the temperature was maintained below 30° C. (external ice-water cooling). After addition was completed, the reaction was stirred at ambient temperature overnight. The 2-trifluoromethyl-3-oxa-2,4,4,5,5,6,6,6-octafluorohexanoyl phosphoric acid ester product was dried in a vacuum oven at 70° C. to give a clear, colorless, viscous liquid. Yield was quantitative.

$^1$H-NMR (400 MHz, acetone-$d_6$): δ 4.80 (m);
$^{19}$F-NMR (376.89 MHz, acetone-$d_6$): −80.6 to −82.5 (m, 8F), −129.4 (m, 2F), −134.7 (dm, 1F).

Example 1

A perfluoroelastomer containing copolymerized monomers of tetrafluoroethylene (TFE), perfluoro(methyl vinyl ether) (PMVE), and perfluoro-8(cyano-5-methyl-3,6-dioxa-1-octene) (8CNVE) was prepared as follows: three aqueous streams were each fed continuously to a 1 liter mechanically stirred, water jacketed, stainless steel autoclave at a rate of 81 cubic centimeters per hour (cc/hr). The first stream consisted of a solution of 35.4 g ammonium persulfate in 3 liters of deaerated, deionized water. The second stream consisted of 180 g of the F(CF$_2$)$_5$—CH$_2$O—PO(OH)$_2$ surfactant and 54 g of Krytox® 157 FSL perfluoropolyether (PFPE) having carboxylate endgroups (available from DuPont) surfactant in 4 liters of deaerated, deionized water. The third stream consisted of 11.8 g sodium hydroxide and 29.3 g of sodium sulfite in 3 liters of deaerated, deionized water. Using a diaphragm compressor, a mixture of TFE (61.7 grams per hour (g/hr)) and PMVE (51.8 g/hr) was fed at constant rate. The temperature was maintained at 75° C., and the pressure at 4.1 MPa (600 psi) throughout the reaction. The polymer emulsion was removed continuously by means of a letdown valve and the unreacted monomers were vented. The polymer was isolated from the emulsion by first diluting it with deionized water at the rate of 8 liters deionized water per liter of emulsion, followed by addition of 320 cc of a magnesium sulfate solution (100 g magnesium sulfate heptahydrate per liter of deionized water) per liter of emulsion at a temperature of 60° C. The resulting slurry was filtered and the polymer solids obtained from a liter of emulsion were re-dispersed in 8 liters of deionized water at 60° C. After filtering, the wet crumb was dried in a forced air oven for 48 hours at 70° C. Polymer yield was 79 g per hour of reactor operation. The polymer composition was 43.9 wt. % PMVE, 1.89 wt. % 8CNVE, the remainder being tetrafluoroethylene. The polymer had an inherent viscosity of 0.51 measured in a solution of 0.1 g polymer in 100 g of solvent consisting of a 60/40/3 volume ratio of heptafluoro-2,2,3-trichlorobutane, perfluoro(butyltetrahydrofuran), and ethylene glycol dimethyl ether at 30° C.

Example 2

A perfluoroelastomer containing copolymerized monomer units of tetrafluoroethylene (TFE), perfluoro(methyl vinyl) ether (PMVE), and perfluoro-8(cyano-5-methyl-3,6-dioxa-1-octene) (8CNVE) was prepared as follows. Three aqueous streams were each fed continuously to a 1 liter mechanically stirred, water jacketed, stainless steel autoclave at a rate of 71 cc/hr. The first stream consisted of 1.6 g ammonium persulfate and 41.3 g of disodium hydrogen phosphate in 1.5 liters of deaerated, deionized (DI) water. The second stream consisted of 45 g of $H(CF_2)_6$—$CH_2O$—$PO(OH)_2$ surfactant and 4.5 g of Krytox® 157 FSL PFPE surfactant in 1.5 liters of deaerated, deionized water. This mixture was prepared by gradually adding the phosphate surfactant to about 600 ml of DI water heated to between 45° C. and 50° C., with stirring, and continuously adjusting the pH to >4.0, using 30 wt. % ammonium hydroxide, as the surfactant was being added. The resulting solution was clear. When all of the phosphate surfactant had been added, the final pH was adjusted to between 6.5 and 7.0. The Krytox® 157 FSL PFPE surfactant was then added and stirred for about 30 min. while maintaining the temperature at 45° C. to 50° C., resulting in a clear, stable solution. DI water was then added to make up the 1.5 liter feed solution. The third stream consisted of 1.6 g ammonium persulfate in 1.5 liters of deaerated, deionized water. Using a diaphragm compressor, a mixture of TFE (47.8 g/hr) and PMVE (58.2 g/hr) was fed at constant rate. The liquid 8CNVE was fed at a rate of 2.9 g/hr. The temperature was maintained at 85° C., the pressure at 4.1 MPa (600 psi), and the pH at 5.9 throughout the reaction. The polymer emulsion was removed continuously by means of a letdown valve and the unreacted monomers were vented. The polymer was isolated from the emulsion by first diluting it with deionized water at the rate of 8 liters deionized water per liter of emulsion, followed by addition of 320 cc of a magnesium sulfate solution (100 g magnesium sulfate heptahydrate per liter of deionized water) per liter of emulsion at a temperature of 60° C. The resulting slurry was filtered and the polymer solids obtained from a liter of emulsion were re-dispersed in 8 liters of deionized water at 60° C. After filtering, the wet crumb was dried in a forced air oven for 48 hours at 70° C. Polymer yield was 106 g per hour of reactor operation. The polymer composition was 48.4 wt. % PMVE, 2.32 wt. % 8CNVE, the remainder being tetrafluoroethylene. The polymer had an inherent viscosity of 0.85 measured in a solution of 0.1 g polymer in 100 g of Flutec® PP-11 (F2 Chemicals Ltd., Preston, UK).

Comparative Example 1

A solution of $(CF_3CF_2CF_2OCF(CF_3)CH_2O)_2PO(OH)$ surfactant (i.e. a diester that is a side product from the preparation of 2-trifluoromethyl-3-oxa-2,4,4,5,5,6,6,6-octafluorohexanoyl phosphoric acid ester) was prepared by gradually adding 20 g of this material to 270 ml deionized (DI) water heated to between 45° C. and 50° C., with stirring, and continually adjusting the pH to >4.0, using 30 wt % ammonium hydroxide, as the surfactant was being added. When all of this phosphate surfactant had been added, the final pH was adjusted to between 6.5 and 7.0. The resulting solution was homogeneous, but turbid. A total of 2 g of Krytox® 157 FSL PFPE surfactant were then added, and the mixture stirred for about 30 min. while maintaining the temperature between 45° C. and 50° C. This mixture was very turbid. The mixture was diluted with an additional 400 ml of DI water, and allowed to cool to room temperature. Krytox® surfactant appeared to separate and form a gelatinous mass. As such, the mixture was considered unusable for a fluoroelastomer polymerization reaction.

Example 3

An aqueous solution was prepared with 27 liters deionized, deoxygenated water, 34.0 g of 2,2,3,3,4,4,5,5,6,6,7,7-dodecafluro-1-heptanephosphoric acid $(H(CF_2)_6$—$CH_2O$—$PO(OH)_2)$, 30.0 g disodium phosphate heptahydrate, and 3 g of ammonium hydroxide. From this solution, 25 liters was charged to a 40 liter reactor. The solution was heated to 80° C. After removal of trace oxygen by purging with nitrogen, the reactor was pressurized with 2101 grams of a mixture of 4.0 wt. % vinylidene fluoride ($VF_2$), 86.0 wt. % hexafluoropropylene (HFP), and 10.0 wt. % tetrafluoroethylene (TFE). At the end of pressurization, the reactor pressure was 2.0 MPa. The reactor was charged with 50.0 ml of an initiator solution of 1 wt. % ammonium persulfate and 5 wt. % disodium phosphate heptahydrate to start polymerization. As the reactor pressure dropped, a mixture of 35.0 wt. % vinylidene fluoride, 37.0 wt. % hexafluoropropylene, and 28.0 wt. % tetrafluoroethylene was fed to the reactor to maintain a 2.0 MPa pressure. After 45 g of this incremental monomer mixture had been fed, 26.0 g of a mixture of 37.29 mol % 1,4-diiodoperfluorobutane, 46.38 mol % 1,6-diiodoperfluorohexane, 11.98 mol % 1,8-diiodoperfluorooctane, and 3.76 mol % 1,10-diiodoperfluorodecane was charged to the reactor. Additional initiator solution was added to maintain the polymerization rate. After 3700 g of the monomer mixture had been added, 4-iodo-3,3,4,4-tetrafluorobutene-1 (ITFB) was introduced to the reactor at a feed rate of 14.5 g ITFB per 3000 g monomer. After a total of 8333 g incremental gaseous monomer had been fed, corresponding to a total of 174 ml initiator solution, 20.4 g ITFB and 18.0 hours, monomer and initiator feed were discontinued. The reactor was cooled and the pressure in the reactor reduced to atmospheric. The resulting fluoroelastomer latex had a solids content of 24.5 wt. % solids, a pH of 3.24, and an average particle diameter of 500 nm, measured by a BI-9000 Particle Size Analyzer, Brookhaven Instruments Corporation. The latex was coagulated with aluminum sulfate solution, washed with deionized water, and dried. The fluoroelastomer had an inherent viscosity of 0.41 dl/g (measured at 30° C. in a solution of 0.1 g polymer/100 g of methyl ethyl ketone), a Mooney viscosity, ML (1+10) at 121° C., of 55.9 and contained 33.8 wt. % $VF_2$, 37.5 wt. % HFP, 28.6 wt. % TFE and 0.245 wt. % I.

Example 4

An aqueous solution was prepared with 27 liters deionized, deoxygenated water, 108.0 g of 2,2,3,3,4,4,5,5,6,6,7-dodecafluro-1-heptanephosphoric acid, 30.0 g disodium phosphate heptahydrate, and 21 g of ammonium hydroxide. From this solution, 25 liters were charged to a 40 liter reactor. The solution was heated to 80° C. After removal of trace oxygen by purging with nitrogen, the reactor was pressurized with 2101 grams of a mixture of 4.0 wt. % vinylidene fluoride ($VF_2$), 86.0 wt % hexafluoropropylene (HFP), and 10.0 wt % tetrafluoroethylene (TFE). At the end of pressurization, the reactor pressure was 2.0 MPa. The reactor was charged with 50.0 ml of an initiator solution of 1 wt. % ammonium persulfate and 5 wt. % disodium phosphate heptahydrate to start polymerization. As the reactor pressure dropped, a mixture of 35.0 wt. % vinylidene fluoride, 37.0 wt. % hexafluoropropylene, and 28.0 wt. % tetrafluoroethylene was fed to the reactor to maintain a 2.0 MPa pressure. After 45 g of this incremental monomer mixture had been fed, 26.0 g of a mixture of 37.29 mol % 1,4-diiodoperfluorobutane, 46.38 mol % 1,6-diiodoperfluorohexane, 11.98 mol % 1,8-diiodoperfluorooctane, and 3.76 mol % 1,10-diiodoperfluorodecane was charged to the reactor. Additional initiator solution was added to maintain polymerization rate. After 3700 g of the monomer mixture had been added, 4-iodo-3,3,4,4-tetrafluorobutene-1 (ITFB) was introduced to the reactor at a feed rate of 14.5 g ITFB per 3000 g monomer. After a total of 8333 g incremental gaseous monomer had been fed, corresponding to a total of 149 ml initiator solution, 20.4 g ITFB and 16.5 hours, monomer and initiator feed were discontinued. The reactor was cooled and the pressure in the reactor reduced to atmospheric. The resulting fluoroelastomer latex had a solids content of 24.5 wt. % solids, a pH of 3.41, and an average particle diameter of 363 nm, measured by a BI-9000 Particle Size Analyzer, Brookhaven Instruments Corporation. The latex was coagulated with aluminum sulfate solution, washed with deionized water, and dried. The fluoroelastomer had an inherent viscosity of 0.42 dl/g (measured at 30° C. in a solution of 0.1 g polymer/100 g of methyl ethyl ketone), a Mooney viscosity, ML (1+10) at 121° C., of 56.0 and contained 34.0 wt. % $VF_2$, 36.4 wt. % HFP, 29.4 wt. % TFE and 0.230 wt. % I.

Example 5

An aqueous solution was prepared with 27 liters deionized, deoxygenated water, 81.0 g of $CF_3CF_2CF_2OCF(CF_3)CH_2OPO(OH)_2$, 14 g ammonium hydroxide, and 30.0 g disodium phosphate heptahydrate. From this solution, 25 liters were charged to a 40 liter reactor. The solution was heated to 80° C. After removal of trace oxygen, the reactor was pressurized with 2445 g of a mixture (initial monomer charge) of 4.0 wt. % vinylidene fluoride ($VF_2$), 86.0 wt. % hexafluoropropylene (HFP), and 10.0 wt. % tetrafluoroethylene (TFE). At the end of pressurization, the reactor pressure was 2.0 MPa. The reactor was charged with 50.0 ml of an initiator solution of 1 wt. % ammonium persulfate and 5 wt. % disodium phosphate heptahydrate to start polymerization. As the reactor pressure dropped, a mixture (incremental monomer feed) of 35.0 wt. % vinylidene fluoride, 37.0 wt. % hexafluoropropylene, and 28.0 wt. % tetrafluoroethylene was fed to the reactor to maintain a 2.0 MPa pressure. After 45 g of this incremental monomer mixture had been fed, 25.0 g of a mixture of 37.29 mol % 1,4-diiodoperfluorobutane, 46.38 mol % 1,6-diiodoperfluorohexane, 11.98 mol % 1,8-diiodoperfluorooctane, and 3.76 mol % 1,10-diiodoperfluorodecane was charged to the reactor. Additional initiator solution was added to maintain polymerization rate. After 3700 g of the incremental monomer mixture had been added, 4-iodo-3,3,4,4-tetrafluorobutene-1 (ITFB) was introduced to the reactor at a feed rate of 14.5 g ITFB per 3000 g monomer. After a total of 8333 g incremental monomer had been fed, corresponding to a total of 263 ml initiator solution, 20.4 g ITFB and 15 hours of elapsed time, monomer and initiator feed were discontinued. The reactor was cooled and the pressure in the reactor reduced to atmospheric. The resulting fluoroelastomer latex had a solids content of 24.1 wt. % solids, and a pH of 3.47. The latex was coagulated with aluminum sulfate solution, washed with deionized water, and dried. The fluoroelastomer had an inherent viscosity of 0.46 dl/g, a Mooney viscosity, ML (1+10) at 121° C., of 64.7 and contained 36.4 wt. % $VF_2$, 35.4 wt. % HFP, 28.2 wt. % TFE and 0.215 wt. % I.

Example 6

A perfluoroelastomer containing copolymerized monomers of tetrafluoroethylene (TFE), perfluoro(methyl vinyl ether) (PMVE), and perfluoro-8(cyano-5-methyl-3,6-dioxa-1-octene) (8CNVE) was prepared as follows: three aqueous streams were each fed continuously to a 1 liter mechanically stirred, water jacketed, stainless steel autoclave at a rate of 81 cubic centimeters per hour (cc/hr). The first stream consisted of 1.13 g ammonium persulfate and 29.67 g of disodium hydrogen phosphate per liter of deaerated, deionized water. The second stream consisted of 89.66 g of $CF_3CF_2CF_2OCF(CF_3)CH_2OPO(OH)_2$ per liter of deaerated, deionized water. The third stream consisted of 1.13 g of ammonium persulfate per liter of deaerated, deionized water. Using a diaphragm compressor, a mixture of TFE (56.3 g/hr) and PMVE (68.6 g/hr) was fed at constant rate. The temperature was maintained at 85° C., the pressure at 4.1 MPa (600 psi), and the pH at 4.9 throughout the reaction. The polymer emulsion was removed continuously by means of a letdown valve and the unreacted monomers were vented. The polymer was isolated from the emulsion by first diluting it with deionized water at the rate of 8 liters deionized water per liter of emulsion, followed by addition of 320 cc of a magnesium sulfate solution (100 g magnesium sulfate heptahydrate per liter of deionized water) per liter of emulsion at a temperature of 60° C. The resulting slurry was filtered, the polymer solids obtained from a liter of emulsion were re-dispersed in 8 liters of deionized water at 60° C. After filtering, the wet crumb was dried in a forced air oven for 48 hr at 70° C. Polymer yield was 124 g per hour of reactor operation. The polymer composition was 48.8 wt. % PMVE, 2.61 wt. % 8CNVE, the remainder being tetrafluoroethylene. The polymer had an inherent viscosity of 0.81 measured in a solution of 0.1 g polymer in 100 g of FLUTEC™ PP11 perfluorocarbon fluid (F2 Chemicals Ltd., Preston, UK) at 30° C.

What is claimed is:
1. An emulsion polymerization process for the production of a fluoroelastomer, said process comprising polymerizing a first monomer selected from the group consisting of vinylidene fluoride, tetrafluoroethylene and perfluoro(methyl vinyl ether) with at least one different monomer in an aqueous medium comprising initiator and at least one dispersing agent to obtain an aqueous dispersion of fluoroelastomer, wherein said dispersing agent is a of the formula $CF_3CF_2CF_2OCF(CF_3)CH_2OPO(OM)_2$, wherein M=a univalent cation.

2. The process of claim 1 wherein said dispersing agent is selected from the group consisting of $CF_3CF_2CF_2OCF(CF)CH_2OPO(OH)_2$ and $CF_3CF_2CF_2OCF(CF_3)CH_2OPO(OH)(ONH_4)$.

3. The process of claim 1 wherein said at least one different monomer is selected from the group consisting of fluoromonomers, hydrocarbon olefins and mixtures thereof.

4. The process of claim 1 wherein said fluoroelastomer comprises copolymerized units selected from the group consisting of i) vinylidene fluoride and hexafluoropropylene; ii) vinylidene fluoride, hexafluoropropylene and tetrafluoroethylene; iii) vinylidene fluoride, hexafluoropropylene, tetrafluoroethylene and 4-bromo-3,3,4,4-tetrafluorobutene-1; iv) vinylidene fluoride, hexafluoropropylene, tetrafluoroethylene and 4-iodo-3,3,4,4-tetrafluorabutene-1; v) vinylidene fluoride, perfluoro(methyl vinyl ether), tetrafluoroethylene and 4-bromo-3,3,4,4-tetrafluorobutene-1; vi) vinylidene fluoride, perfluoro(methyl vinyl ether), tetrafluoroethylene and 4-iodo-3,3,4,4-tetrafluorobutene-1; vii) vinylidene fluoride, perfluoro(methyl vinyl ether), tetrafluoroethylene and 1,1,3,3,3-pentafluoropropene; viii) tetrafluoroethylene, perfluoro(methyl vinyl ether) and ethylene; ix) tetrafluoroethylene, perfluoro(methyl vinyl ether), ethylene and 4-bromo-3,3,4,4-tetrafluorobutene-1; x) tetrafluoroethylene, perfluoro (methyl vinyl ether), ethylene and 4-iodo-3,3,4,4-tetrafluorobutene-1; xi) tetrafluoroethylene, propylene and vinylidene fluoride; xii) tetrafluoroethylene and perfluoro(methyl vinyl ether): xiii) tetrafluoroethylene, perfluoro(methyl vinyl ether) and perfluoro(8-cyano-5-methyl-3,6-dioxa-1-octene); xiv) tetrafluoroethylene, perfluoro(methyl vinyl ether) and 4-bromo-3,3,4,4-tetrafluorobutene-1; xv) tetrafluoroethylene, perfluoro(methyl vinyl ether) and 4-iodo-3,3,4,4-tetrafluorobutene-1; xvi) tetrafluoroethylene, perfluoro (methyl vinyl ether) and perfluoro(2-phenoxypropyl vinyl) ether; and xvii) tetrafluoroethylene and propylene.

5. An emulsion polymerization process of claim 1 further comprising the introduction of a second dispersing agent, said second dispersing agent being a perfluoropolyether having at least one endgroup selected from the group consisting of carboxylic acid, carboxylic acid salt, sulfonic acid, sulfonic acid salt, phosphoric acid and phosphoric acid salt.

* * * * *